United States Patent [19]

Arvanitis et al.

[11] Patent Number: 5,380,755

[45] Date of Patent: Jan. 10, 1995

[54] ALKYL AND ALKYLBENZYL ETHERS OF SUBSTITUTED HYDROQUINONES

[75] Inventors: Argyrios G. Arvanitis, Kennett Square, Pa.; Everett L. Scholfield, Wilmington, Del.

[73] Assignee: The Du Pont Merck Pharmaceutical Company, Wilmington, Del.

[21] Appl. No.: 918,836

[22] Filed: Jul. 24, 1992

[51] Int. Cl.$^6$ ............................................. A61K 31/275
[52] U.S. Cl. ................................... 514/522; 568/306; 568/442; 568/331; 568/275; 568/405; 568/406; 568/404; 568/408; 568/410; 560/53; 560/173; 564/347; 564/171; 514/521; 514/523; 514/512; 514/545; 514/533; 514/534; 514/680; 514/699; 514/617; 514/620; 514/621; 514/622; 514/651
[58] Field of Search ....................... 568/331, 306, 442; 514/522, 521, 523, 512, 545, 533, 534, 680, 699, 617, 620, 621, 622, 651; 558/275, 405, 406, 404; 560/53, 173; 564/347, 171

[56] References Cited

U.S. PATENT DOCUMENTS

| | | | |
|---|---|---|---|
| 4,060,633 | 11/1977 | Gante et al. | 568/331 |
| 4,202,978 | 5/1980 | Fahrenholtz et al. | 568/642 |
| 4,329,367 | 5/1982 | Francis | 562/441 |
| 4,425,362 | 1/1984 | Barthold et al. | 514/521 |
| 4,649,160 | 3/1987 | Machin | 568/331 |
| 4,971,995 | 11/1990 | Schoofs et al. | 568/331 |

FOREIGN PATENT DOCUMENTS 9011997 10/1990 WIPO ................................. 568/331

Primary Examiner—James H. Reamer
Attorney, Agent, or Firm—Gerald J. Boudreaux

[57] ABSTRACT

The present invention provides alkyl and alkylbenzyl ethers of substituted hydroquinones and pharmaceutical compositions containing them. The present invention further provides methods of using these compounds and compositions to inhibit monoamine oxidase, particularly monoamine oxidase B. The present invention further provides methods for the treatment of diseases involving monoamine oxidase.

12 Claims, No Drawings

ALKYL AND ALKYLBENZYL ETHERS OF SUBSTITUTED HYDROQUINONES

The present invention relates to alkyl and alkylbenzyl ethers of substituted hydroquinones and pharmaceutical compositions containing them. The present invention further relates to methods of using these compounds and compositions to inhibit monoamine oxidase, and to treat diseases mediated by monoamine oxidase.

BACKGROUND OF THE INVENTION

The mitochondrial enzymes monoamine oxidase (MAO) catalyze the oxidative deamination of a number of biogenic and xenobiotic amines and regulate the concentration of these amines in brain and peripheral tissues. This activity produces ammonia, aldehydes and hydrogen peroxide, which are agents with established or potential toxicity. In the brain MAO is active in both neurons and glial cells.

In 1968 Jonston discovered that MAO exists in two forms, termed MAO A and MAO B, with different substrate specificities and inhibitor sensitivities (Jonston, J. P., Biochem. Pharmacol., 1968, 17, 1285). Recently, different cDNA clones have been isolated from the human liver encoding the A and B forms of MAO. It has been shown that MAO A and MAO B differ in primary structure with about 70% homology (Bach, A. W. J., Johnson, D. L., Abell, C. W., Bembenek, M. E., Kwan, S-W., and Shih, J. C., Proc. Natl. Acad. Sci, USA, 85:4934–4938; Shih, J. C. Neuropharm., 1991, 4, 1).

In humans, MAO A is predominantly located in the outer mitochondrial membrane of aminergic neurons but also found in the gut and placenta, while MAO B is the form found exclusively in platelets and is the major form present in liver and glial cells. MAO A primarily metabolizes norepinephrine and serotonin, whereas MAO B preferentially oxidizes dopamine (Murphy, D. L., Garrick, N. A., Aulakh, C. S., and Cohen, R. M., J. Clin. Psychiat., 1984, 45, 37). Inhibition of MAO A prevents the metabolism of catecholamines leading to an increased level of norepinephrine in the adrenergic neurons. Selective MAO B inhibition leading to an increased level of dopamine would decrease the extra-pyramidal side effects associated with other MAO inhibitors. This would potentially eliminate the possibility of exaggerated responses, including severe headaches, hypertension (possible hypertensive crisis), and cardiac arrhythmias caused by the intake of tyramine containing foods (Ilett, K. F., George, C. F., and Davies, D. S. Biochem. Pharmacol., 1980, 29, 2551).

In humans, where dopamine is predominantly metabolized by MAO B, inhibitors of this isozyme should have utility as an adjunct to L-dopa in the treatment of Parkinson's disease, as well as in the treatment of Alzheimer's disease as cognitive enhancers.

The clinical use of long-acting irreversible MAO inhibitors of the old generation was hampered by their hepatotoxic and hypertensive effects as mentioned above. This fact and the potential of new therapeutic uses for MAO inhibitors has caused a renewed effort in discovering reversible and selective inhibitors both of A and B type.

Two good examples of this effort are the MAO inhibitors described by Schoofs et al. in U.S. Pat. No. 4,971,995 and by Renaut et al. in Foreign Patent No. WO90/11997 containing an unsubstituted hydroquinone ring. A subsistuent on this ring, especially electron withdrawing, provides an extended conjugated system with either of the oxygens on that ring. This can interact better with the flavin portion on the enzymatic active site. Furthermore it provides an extra interaction point with this site which increases both activity and selectivity between the two enzymes MAO A and MAO B.

It is an objective of this invention to provide compounds possessing the valuable pharmacological capability of inhibiting monoamine oxidases, and monoamine oxidase B in particular. It is a further objective of the present invention to provide methods of treating neurological disorders including but not limited to memory disorders, cognitive dysfunction, dementia, dementia of the Alzheimer's type, Parkinson's syndrome, depression, hyperactive syndrome, schizophrenia, and changes in temperament.

SUMMARY OF THE INVENTION

The present invention provides compounds of formula:

and pharmaceutically acceptable salts thereof, wherein:

X is $C_2$–$C_6$ alkyl, a $C_4$–$C_{12}$ cycloalkyl, $C_2$–$C_6$ alkenyl, $C_2$–$C_6$ alkynyl, or $R^1$, $R^2$, and $R^3$ are independently selected from the group including hydrogen, halogen, $C_1$–$C_4$ alkyl, $C_1$–$C_4$ alkoxy, $CF_3$, $C_2F_5$, CN, and $NO_2$;

A and D are independently selected from the group including hydrogen, $COR^5$, $CH_2OR^6$ $CONR_2^6$ and CN, provided that A and D cannot both be H;

Y is a nitrogen or oxygen atom;

$R^4$ and $R^{4'}$ are independently selected from the group including hydrogen, $C_1$–$C_4$ alkyl, allyl, propargyl, and $COR^8$, provided that when Y is oxygen $R^4$ is hydrogen or $COR^8$, and $R^{4'}$ is not present;

Z is hydrogen, CN, OH, $OR^6$, $OCOR^6$, $OCO_2R^6$, or $OCONR^6R^7$;

$R^5$ is hydrogen, $C_1$–$C_4$ alkyl, or $C_1$–$C_4$ alkoxy, or $C_1$–$C_4$ dialkylamino;

$R^6$ and $R^7$ independently are selected from the group including hydrogen and $C_1$–$C_4$ alkyl;

$R^8$ is $C_1$–$C_4$ alkyl, $C_1$–$C_4$ alkoxy, or $C_1$–$C_4$ alkylamino, or $C_2$–$C_8$ dialkylamino;

m is 0 or 1; and n is 1–5, provided that when n=2–5, then m=0; provided that when:

$R^1$, $R^2$, and $R^3$ are H,

A is H,

D is $CO_2CH_3$, $COCO_2H$, $COCH_3$, CN, or $CONH_2$, n=0–3, and
m=0, then
Z cannot be $CO_2CH_2CH_3$, $CO_2H$, or $OCH_3$.

The present invention also provides a method of inhibiting monoamine oxidases in a mammal and a method of treating diseases mediated by monoamine oxidases in a mammal comprising administering to a mammal in need of such inhibition and/or treatment an effective amount of a compound of formula:

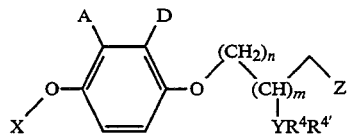
(I)

and pharmaceutically acceptable salts thereof, wherein:

X is $C_2-C_6$ alkyl, $C_4-C_{12}$ cycloalkyl, $C_2-C_6$ alkenyl, $C_2-C_6$ alkynyl, or

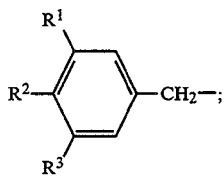

$R^1$, $R^2$, and $R^3$ are independently selected from the group including hydrogen, halogen, $C_1-C_4$ alkyl, $C_1-C_4$ alkoxy, $CF_3$, $C_2F_5$, CN, and $NO_2$;

A and D are independently selected from the group including hydrogen, $COR^5$, $CH_2OR^6$, $CONR_2^6$ and CN, provided that A and D cannot both be H;

Y is a nitrogen or oxygen atom;

$R^4$ and $R^{4'}$ are independently selected from the group including hydrogen, $C_1-C_4$ alkyl, allyl, propargyl, and $COR^8$, provided that when Y is oxygen $R^4$ is hydrogen or $COR^8$, and $R^{4'}$ is not present;

Z is hydrogen, CN, OH, $OR^6$, $OCOR^6$, $OCO_2R^6$, or $OCONR^6R^7$;

$R^5$ is hydrogen, $C_1-C_4$ alkyl, or $C_1-C_4$ alkoxy, or $C_1-C_4$ dialkylamino;

$R^6$ and $R^7$ independently are selected from the group including hydrogen and $C_1-C_4$ alkyl;

$R^8$ is $C_1-C_4$ alkyl, $C_1-C_4$ alkoxy, or $C1-C4$ alkylamino, or $C_2-C_8$ dialkylamino;

m is 0 or 1; and n is 1–5, provided that when n=2−5, then m=0.

Preferred Embodiments

Preferred compounds are compounds of formula (I) wherein:

X is

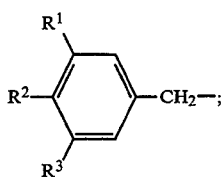

provided that when m=0 and Z is $CO_2R^6$ or $OR^6$, then $R^6$ is not $C_1-C_4$ alkyl.

Most preferred compounds are those compounds of formula (I) wherein:

$R^1$, $R^2$, and $R^3$ are independently selected from the group including H, F, Cl, Br, I, $CH_3$, $OCH_3$, $CF_3$, CN, and $NO_2$;

A and D are independently selected from the group including H, $COR^5$, $CONR_2^6$, and $CH_2OR^6$, provided that either A or D is H and that A and D cannot both be H;

Y is a nitrogen or oxygen atom;

$R^4$ and $R^{4'}$ are independently selected from the group including H, $CH_3$, propargyl, and $COR^8$, provided that when Y is oxygen $R^4$ is H or $COR^8$, and $R^{4'}$ is not present;

Z is H, CN, OH, $OCOR^6$, $OCO_2R^6$, or $OCONR^6R^7$;

$R^5$ is H, $CH_3$, $C_2H_5$, $OCH_3$, $OC_2H_5$, $N(CH_3)_2$, $N(C_2H_5)_2$;

$R^6$ is H, $CH_3$, or $C_2H_5$;

$R^8$ is $CH_3$, $C_2H_5$, $OCH_3$, $OC_2H_5$, $N(CH_3)_2$, $N(C_2H_5)_2$;

m is 0 or 1;

n is 1–5, provided that when n=2–5, then m=0.

DETAILED DESCRIPTION OF THE INVENTION

Compounds of the present invention may be prepared by methods disclosed herein. For example, compounds of formula (I) wherein m=0 may be prepared via the method shown in Scheme I. In this method, a compound of formula (1), wherein L is a leaving group such as Cl, Br, I, mesylate, tosylate or triflate, is reacted with a hydroquinone of formula (2) in a suitable solvent in the presence of a suitable base to give a monoalkylated intermediate of formula (3). The monoalkylated intermediate of formula (3) is then itself alkylated with a compound of formula L—$(CH_2)_n CH_2 Z$ in a suitable solvent in the presence of a suitable base to give (4) which is a compound of formula (I) wherein m=0.

Scheme I

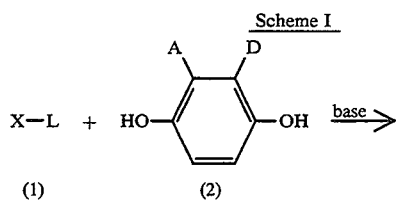

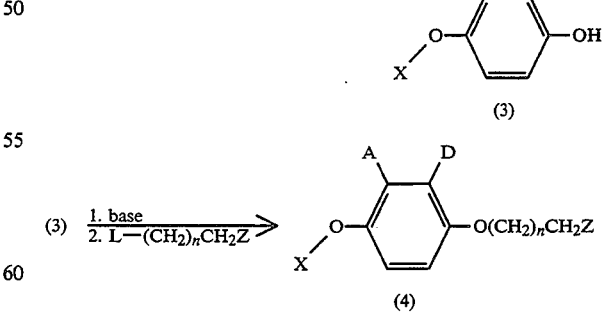

Compounds of formulae (1) and (2) may be obtained commercially or may be prepared from commercially available starting materials using techniques well known to those skilled in the art of organic synthesis. Suitable bases for each reaction include metal carbonates and hindered amines. The preferred base is potassium carbonate. Suitable solvents for each reaction include $C_1$-$C_6$ nitriles, $C_1$-$C_6$ ethers, $C_1$-$C_6$ amides, and $C_1$-$C_6$ alcohols. The preferred solvent is acetonitrile. The reactions may be carried out at a temperature between 0°–150° C. The preferred reaction temperature is between 20°–100° C. The reactions are carried out for a time period between 5 minutes and 24 hours. The preferred reaction time is between 2–24 hours. The preferred method for the conversion of (3) to (4) includes addition of potassium iodide to the reaction mixture. If desired, the intermediate (3) and the final product (4) can be further purified using conventional synthetic techniques including distillation, chromatography and recrystallization.

The method of Scheme I is versatile and is capable of modification to give other compounds of formula I. For example, Scheme II shows a method derived from Scheme I for the synthesis of compounds of formula (I) where X is a substituted benzyl, A is H, and D is $CH_2OH$ or CHO.

D is $CH_2OH$, and m=0. Compound (9) can be further manipulated to give additional compounds of formula (I). For example, reaction of (9) with an oxidizing agent such as chromium oxide affords aldehydes of formula (10). Compound of formula (10) are compounds of formula (I) wherein X is benzyl, A is H, D is CHO, and m=0. The compounds of formula (I) obtained from this route may be further purified using conventional synthetic techniques including distillation, chromatography and recrystallization.

Scheme III shows an alternative method for the synthesis of compounds of formula (I). In this method Scheme III

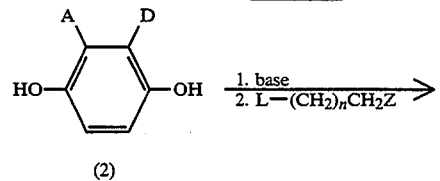

(2)

Scheme II

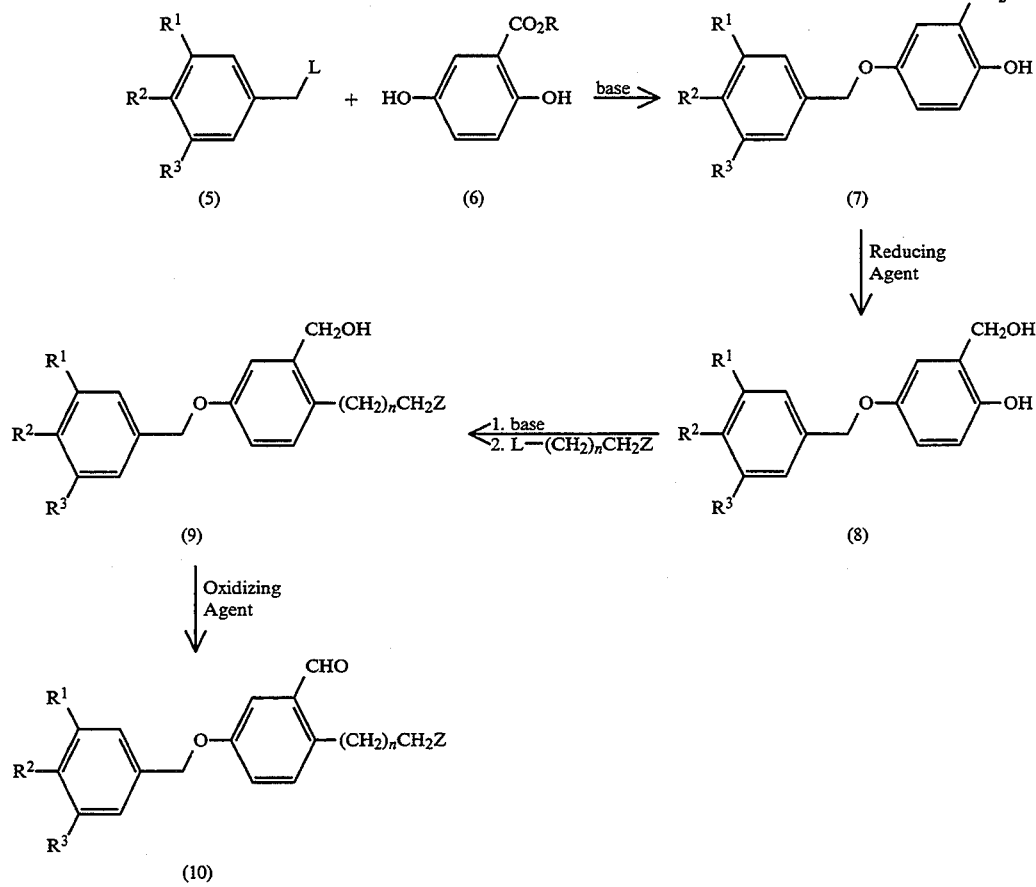

In this method, compound of formula (5), wherein L is as defined in Scheme I, is reacted with the hydroquinone (6) in a solvent in the presence of a base to give an intermediate of formula (7). Intermediate (7) is then reacted with a reducing agent such as lithium aluminum hydride, in a solvent such as ether or tetrahydrofuran, to give the alcohol intermediate (8). Intermediate (8) is then reacted with a compound of formula $L-(CH_2)_nCH_2Z$ in a suitable solvent in the presence of a suitable base to give (9). Compound (9) is a compound of formula (I) wherein X is a substituted benzyl, A is H,

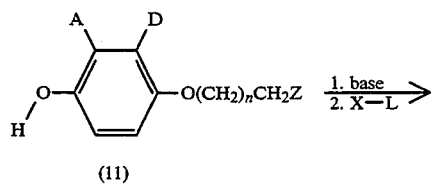

(11)

-continued
Scheme III

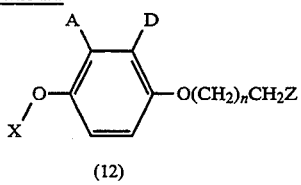

(12)

a compound of formula (2) is first reacted with a compound of formula L—(CH$_2$)$_n$CH$_2$Z in a suitable solvent in the presence of a suitable base to give intermediate (11). Intermediate (11) is then reacted with a compound of formula X-L in a suitable solvent in the presence of a suitable base to give (12) which is a compound of formula (I) wherein m=0. The definition of L and the reaction parameters for the method of Scheme III are the same as described for the method of Scheme I.

Scheme IV shows a method for the synthesis of compounds of formula (I) wherein n=1, m=1, X is a substituted benzyl, Z is H, and Y is NR$^4$R$^{4'}$.

ture. The amines of formula HNR$^4$R$^{4'}$ are commercially available or may be prepared using standard methods.

Scheme V shows a method for the synthesis of compounds of formula (I) wherein n=1, m=1, Y is oxygen, and Z is CN, OH, or OR$^6$. In the first step of this method, a compound of formula (3) is reacted with an epoxide of formula (16), utilizing the reaction conditions described in the first step of Scheme I, to give intermediate compound (17). In this method, L has the same definition as in Scheme I. The epoxide, (16), is commercially available or can be prepared using standard techniques. In the second step of Scheme V, intermediate (17) is reacted in a suitable solvent with M$^+$Z$^-$ to give (18) which is a compound of Formula (I) wherein n=1, m=1, Y is oxygen, and Z is CN, OH, or OR$^6$. M$^+$ is a metal cation such as potassium or sodium. Z$^-$ is —OH, —CN, or —OR$^6$. Suitable solvents include acetonitrile, dimethylformamide, tetrahydrofuran, dimethylsulfoxide, glyme, diglyme and HOR$^6$. The reaction may be carried out at a temperature between 0°–150° C. The preferred reaction temperature is between 20°–120° C. The reaction may be conducted over

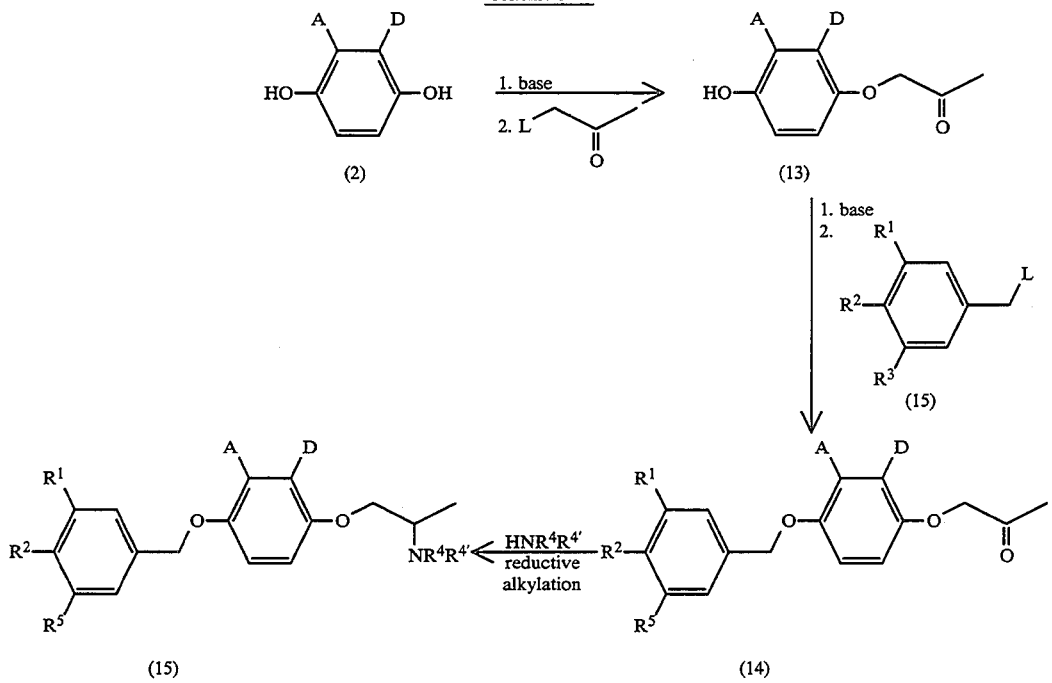

In the first step of this method, a hydroquinone of formula (2) is reacted with a ketone bearing a leaving group, L, in a suitable solvent in the presence of a suitable base to give a compound of formula (13). For this step, the definition of L and the reaction conditions are the same as described for the first step of the method of Scheme I. The alkylated hydroquinone (13), is reacted with a compound of formula (5) under the reaction conditions described for step 1 of the method of Scheme I, to give a compound of formula (14). The ketone (14) is then reacted with an amine of formula HNR$^4$R$^{4'}$ under reductive amination conditions to give a compound of formula (15) which is a compound of formula (I) wherein X is substituted benzyl, Y is NR$^4$R$^{4'}$ and Z is H. There are many methods available for the reductive amination of the ketone intermediate (14). The preferred method utilizes sodium cyanoborohydride and zinc chloride in an aqueous/alcoholic solvent mixa time range of 5 minutes to 48 hours. The preferred reaction time is 4–24 hours. The intermediates and final products may be further purified, if desired, using standard techniques such as distillation, chromatography and recrystallization.

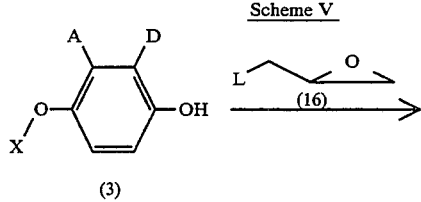

-continued
Scheme V

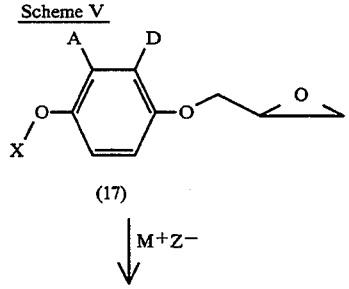

(17)

↓ M⁺Z⁻

Such reagents are commercially available or may be prepared using standard techniques. The transformation of (23) to (24) is accomplished using reaction conditions effective for the acylation of alcohols. Such conditions are well known to those skilled in the art of organic synthesis. The chiral tosyl epoxides (21) can be prepared according to the procedure described by J. M. Klunder, S. Y. Ko and K. B. Sharpless, J. Org. Chem., 1986, 51, 3710 and J. M. Klunder, T. Onami, and K. B. Sharpless, J. Org. Chem., 1989, 54, 1295). These references also disclose alternative procedures for the transformation of (3) to (17) and (23) to (24).

Scheme VI

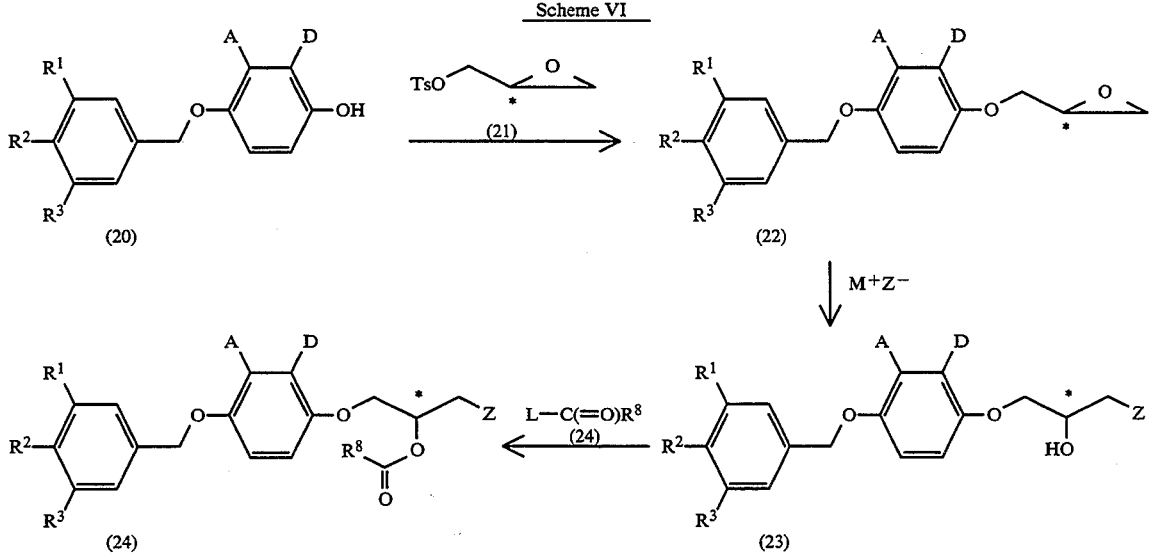

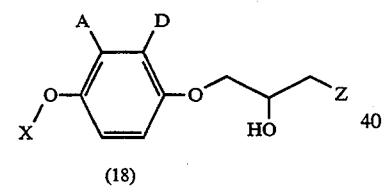

(18)

Scheme VI shows a method for the prepartion of compounds of formula (I) wherein n=1, m=1, X is a substituted benzyl, Y is oxygen, and Z is CN, OH, or $OR^6$. In the first step of this method, phenol intermediate (20), prepared as described for phenol intermediate (7) in Scheme II, is reacted with the chiral tosyl epoxide (21) to give the chiral intermediate (22). This reaction is carried out as described for the first step of Scheme V. The epoxide of intermediate (22) is then opened via reaction with M⁺Z⁻ to give compound (23) which is a compound of formula (I) wherein n=1, m=1, X is a substituted benzyl, Y is OH and Z is CN, OH, or $OR^6$. The reagent M+Z⁻ is as defined for the method of Scheme V, and, the reaction conditions utilized to transform (22) to (23) are as described in Scheme V for the transformation of (17) to (18). Compound (23) is then further elaborated to give other compounds of formula (I). For example, reaction of (23) with a reagent such as L—C(=O)$R^8$ in a suitable solvent and in the presence of a tertiary amine affords compounds of formula (24) which are compounds of formula (I) wherein n=1, m=1, X is a substituted benzyl, Y is oxygen, $R^4$ is $COR^8$, $R^{4'}$ is not present, and Z is CN, OH, or $OR^6$. Reagents such as L—C(=O)$R^8$ are typically chloroacyls, chloroformate esters, or chlorocarbamyl esters.

Scheme VII shows a method for the preparation of intermediates useful in the synthesis of compounds of formula (I).

Scheme VII

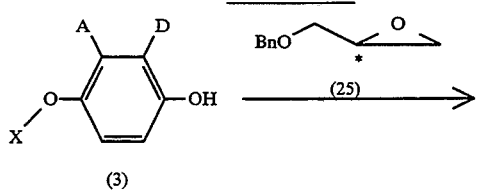

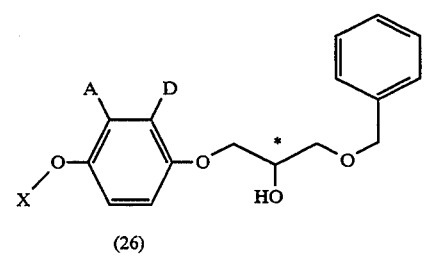

(26)

In this method, intermediate (3) is reacted with the benzyloxy chiral epoxide (25) to give intermediate (26). The preparation of (25) is disclosed by S. Takano, M. Akiyama and K. Ogasawara, Synthesis, 1985, 503 which is hereby incorporated by reference. This reference also discloses reaction conditions which may be used for the reaction of (3) with (25) to give (26). Intermediate (26) may then be further elaborated. The hydroxy group on the asymmetric carbon atom may be converted to another functional group, eg. acyl, ether, amino, using techniques well known to those skilled in the art of organic synthesis.

Scheme VIII shows an alternative method for the preparation of compounds having the structures (23) or (24), utilizing the newly discovered asymmetric hydroxylation process reported by K. B. Sharpless, W. Amberg, Y. L. Bennani, G. A. Crispino, J. Hartung, K.-S. Jeong, H.-L. Kwong, K. Morikawa, Z.-M. Wang, D. Xu, and X.-L. Zhang, J. Org. Chem., 1992, 57, 2768.

EXAMPLE 1

4-[2'-Formyl-4'-(m-chlorophenylmethyloxy)phenoxy]-butyronitrile (1)

2,5-Dihydroxybenzoic acid, 30 grams (0.195 moles), was heated to reflux with 10 ml conc'd. sulphuric acid in 500 ml methanol for 72 hours. Then it was neutralized with solid sodium bicarbonate and striped in vacuo. The product was extracted with ethyl acetate and the organic extract was dried and stripped in vacuo to give 29.8 grams of methyl 2,5-dihydroxybenzoate of >90%

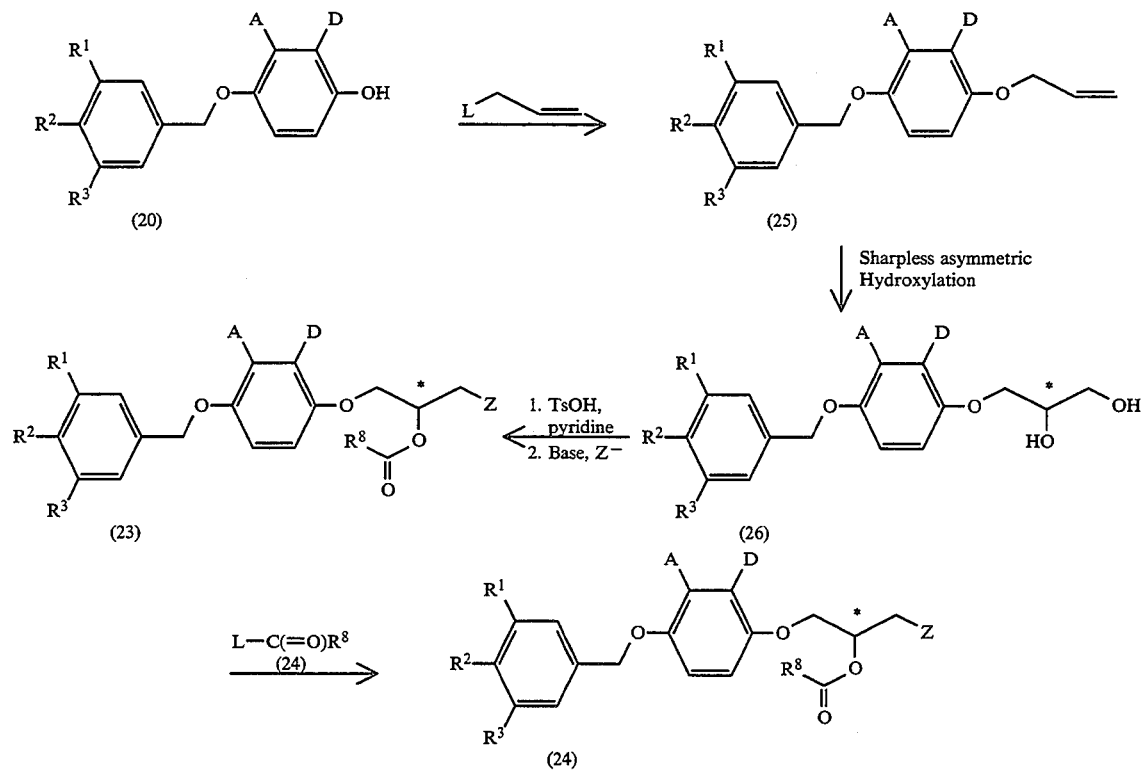

In this scheme the monoalkylated hydroquinone (20) is treated with allyl chloride or bromide in the presence of an appropriate base to give the corresponding allyl ether (25). This is then asymmetrically hydroxylated by the method described by Sharpless et. al. to give the corresponding diol (26). This is then treated with the appropriate base, such as NaH, to give the chiral epoxide intermediate, which is opened by the nucleophile Z⁻ to afford compounds of the general formula (23).

Finally enantiomers of compounds of formula (I) prepared via the non-chiral procedures discussed above can be synthesized by classical separation of the corresponding racemic mixtures.

EXAMPLES

The following non-limiting examples describe the invention in greater detail. All reactions requiring anhydrous conditions are performed under an atmosphere of nitrogen. Concentration under reduced pressure is performed with a rotary evaporator using a water aspirator. Unless otherwise indicated, standard laboratory procedures known to those skilled in the art of organic chemistry are followed.

purity.

Eight grams (47.62 mmoles) of the above ester was treated with 6.3 ml (47.62 mmoles) of 3-chlorobenzyl bromide and 8 grams potassium carbonate in 70 ml acetonitrile under reflux for 4 hours. The mixture was diluted with 100 ml ethyl acetate, filtered, and stripped in vacuo. The residue was recrystallized from ethanol to give 9.5 g of 2-Carbomethoxy-4-(m-chlorophenylmethyloxy)-phenol (62% yield from 2,5-dihydroxybenzoic acid).

2-Carbomethoxy-4-(m-chlorophenylmethyloxy)-phenol, 1.6 grams (5.31 mmoles), was treated with 330 mg (8.67 mmoles) of lithium aluminum hydride in 50 ml dry tetrahydrofuran at 25° C. for 16 hours. The mixture was quenched with water, acidified with 70 ml 1M hydrochloric acid, and extracted with ethyl acetate. The extracts were dried and stripped in vacuo to give 1.5 grams of product 2-Hydroxymethyl-4-(m-chlorophenylmethyloxy)-phenol.

2-Hydroxymethyl-4-(m-chlorophenylmethyloxy)-phenol, 2.8 grams (10.5 mmoles) was treated with 1.3 ml (13.1 mmoles) of 4-bromobutyronitrile, 2.8 grams potassium carbonate and 220 mg of potassium iodide in 50 ml acetonitrile under reflux for 48 hours. Then the solids were filtered off and the filtrate was concentrated and chromatographed on silica gel using 1:2 ethyl acetate/hexanes and 1:1 ethyl acetate/hexanes as eluent to give 2.62 grams product (75% yield).

The above product, 2.62 grams (7.9 mmoles), was treated with a mixture of 2.6 grams pyridinium chlorochromate and 2.6 grams celite in 100 ml dry methylene chloride for 2.5 hours. Then the mixture was diluted with 100 ml ether and filtered through florisil. The filtrate was stripped in vacuo and the residue was chromatographed on silica gel using 1:3 ethyl acetate/hexanes as eluent to give 1.95 grams of product 4-[2'-Formyl-4'-(m-chlorophenylmethyloxy)phenoxy]butyronitrile (75% yield). Mp 75°–77° C. Elemental analysis. Calculated for $C_{18}H_{16}ClNO_3$: C 65.55, H 4.89, N 4.25, Cl 10.75; found: C 65.58, H 4.89, N 4.18, Cl 10. 48.

EXAMPLE 2

4-]2'-Methoxymethyl-4'-(m-chlorophenylmethyloxy)phenoxy]butyronitrile (2)

2-Hydroxymethyl-4-(m-chlorophenylmethyloxy)phenol, 280 mg (0.84 mmoles), was treated with 40 mg (1 mmole) 60% sodium hydride in oil in 5 ml dry tetrahydrofuran and then with 0.062 ml iodomethane at 25° C. for 20 hours. Then the solvent was stripped off and the residue was chromatographed on silica gel using 1:2 ethyl acetate/hexanes to give 160 mg product (3) at 55% yield. Mp 66°–68° C. Elemental analysis. Calculated for $C_{19}H_{20}ClNO_3$: C 65.99, H 5.83, N 4.05, Cl 10.02; found: C 66.10, H 5.79, N 3.97, Cl 10.02.

EXAMPLE 3

4-[2'-Carbomethoxy-4'-(m-chlorophenylmethyloxy)phenoxy]butyronitrile (3)

2-Carbomethoxy-4-(m-chlorophenylmethyloxy)phenol, 1 gram (3.32 mmoles), was treated with 1 gram potassium carbonate, 0.4 ml 4-bromobutyronitrile, and 70 mg potassium iodide in 18 ml acetonitrile under reflux for 64 hours. Then the mixture was filtered and the filtrate was stripped in vacuo. The residue was chromatographed on silica gel using 1.3 ethyl acetate/hexanes to give 0.97 grams of the title product at 79% yield. Mp 97°–98° C. Elemental analysis. Calculated for $C_{19}H_{18}ClNO_4$: C 63.42, H 5.04, N 3.89, Cl 9.85; found: C 63.38, H 5.01, N 3.81, Cl 9.77.

EXAMPLE 4

4-[2'-Acyl-4'-(m-chlorophenylmethyloxy)phenoxy]butyronitrile (4)

2,5-Dihydroxyacetophenone, 5 grams (32.9 mmoles), was treated with 4.5 ml 3-chlorobenzyl bromide and 5 grams potassium carbonate in 60 ml acetonitrile under reflux for 5 hours. Then the mixture was diluted with 100 ml ethyl acetate and filtered. The filtrate was stripped in vacuo and the residue was recrystallized from ethanol to give 6.2 grams of product 2-acetyl-4-(m-chlorophenylmethyloxy)-phenol at 68% yield.

2-Acetyl-4-(m-chlorophenylmethyloxy)-phenol, 1.5 grams (3.6 mmoles), was treated with 0.5 ml 4-bromobutyronitrile, 1.2 grams potassium carbonate and 84 mg potassium iodide in 25 ml acetonitrile under reflux for 25 hours. Then the solids were filtered off and the filtrate was stripped in vacuo. the residue was chromatographed on silica gel using 1:3 ethyl acetate/hexanes to give 1.35 grams product (5) at 80% yield. Mp 65°–66° C. Elemental analysis. Calculated for $C_{19}H_{18}ClNO_3$: C 66.37, H 5.28, N 4.07, Cl 10.31; found: C 66.28, H 5.18, N 4.07, Cl 10.15.

EXAMPLE 5

4-[3'-Acyl-4'-(m-chlorophenylmethyloxy)phenoxy]butyronitrile (5)

2,5-Dihydroxyacetophenone, 2 grams (13.15 mmoles), was treated with 1.31 ml (13.15 mmoles) 4-bromobutyronitrile and 1.5 grams potassium carbonate in 35 ml acetonitrile under reflux for 20 hours. Then the solids were filtered off, the filtrate stripped in vacuo, and the residue was chromatographed on silica gel using methylene chloride of a as eluent to give 2.25 grams of 3-acyl-4-(m-chlorophenylmethyloxy)phenol at 78% yield.

3-Acyl-4- (m-chlorophenylmethyloxy)phenol, 0.5 grams (2.28 mmoles), was treated with 0.42 ml (2.99 mmoles) of 3-chlorobenzylbromide and 0.5 grams potassium carbonate in 15 ml acetonitrile under reflux for 20 hours. Then the solids were filtered off and the filtrate was stripped in vacuo. The residue was chromatographed on silica gel using 1:2 ethyl acetate/hexanes to give 680 mg of product (7) at 87% yield. Elemental analysis. Calculated for $C_{19}H_{18}ClNO_3$: C 66.37, H 5.28, N 4.07, Cl 10,31; found: C 66.20, H 5.21, N 3.96, Cl 10.19.

EXAMPLE 6

4-{2'-Acetyl-4'-[(3,5-trifluoromethylphenyl)methyloxy]phenoxy}-butyronitrile (6)

2,5-Dihydroxyacetophenone, 1 gram (6.57 mmoles), was treated with 1.2 ml (6.51 mmoles) of 3,5-bis(trifluoromethyl)benzyl bromide and 1.8 grams potassium carbonate in 50 ml acetonitrile at 25° C. for 24 hours. The mixture was stripped in vacuo. The residue was partitioned between 30 ml 1M sodium hydroxide and 60 ml ethyl acetate. The organic layer was dried over anhydrous magnesium sulfate and the solvent was stripped in vacuo. The residue was recrystallized from ethanol to give 1.58 grams of 2-acetyl-4-[(3,5-trifluoromethylphenyl)methyloxy]-phenol at 64% yield.

2-Acetyl-4-[(3,5-trifluoromethylphenyl)methyloxy]-phenol, 1.58 grams (4.18 mmoles), was treated with 0.42 ml (4.18 mmoles) 4-bromobutyronitrile, and 1.44 grams (10.45 mmoles) potassium carbonate in 50 ml acetonitrile under reflux for 32 hours. The mixture was cooled to room temperature. The solvent was stripped in vacuo and the residue was partitioned between 30 ml 1M sodium hydroxide and 2×60 ml ethyl acetate. The organic layers were combined and dried over anhydrous magnesium hydroxide. The solvent was stripped in vacuo. The residue was chromatographed on silica gel using 1:3 ethyl acetate hexanes as eluent to give 0.59 grams product (16) at 32% yield, mp 110°–112° C. Elemental analysis. Calculated for $C_{21}H_{17}F_6NO_3$: C 56.64, H 3.85, N 3.14, F 25.59; found: C 56.98, H 3.86, N 3.05, F 25.31.

EXAMPLE 7

3-[2'-Acyl-4'-(m-trifluoromethylphenylmethyloxy)phenoxy]propanol (7)

2,5-Dihydroxyacetophenone, 4 grams (26.13 mmoles) was treated with 4 ml (26.13 mmoles) 3-trifluoromethylbenzyl bromide and 4 grams potassium carbonate in 60 ml acetonitrile under reflux for 5 hours. Then the mixture was diluted with 100 ml ethyl acetate, filtered, and the filtrate was stripped in vacuo. The residue was recrystallized from ethanol to give 5.2 grams of 2-acyl-4-(m-trifluoromethylphenylmethyloxy)-phenol at 64% yield.

2-Acyl-4-(m-trifluoromethylphenylmethyloxy)-phenol, 1.5 grams (4.83 mmoles), was treated with 0.53 ml (5.94 mmoles) 3-bromopropanol, 1.5 grams potassium carbonate, and 183 mg potassium iodide in 16 ml acetonitrile under reflux for 50 hours. Then the mixture was diluted with 20 ml ethyl acetate, filtered, and the filtrate was stripped in vacuo. The residue was chromatographed on silica gel using 1:1 ethyl acetate/hexanes, to give 1.52 grams product (23) at 85% yield. Mp 60°–62° C. Elemental analysis. Calculated for $C_{19}H_{19}F_3O_4$: C 61.95, H 5.20, F 15.47; found: C 61.79, H 5.09, F 15.70.

EXAMPLE 8

N-2-[3'-Acyl-4'-(m-chlorophenylmethyloxy)phenoxy]-1-methylethyl-N-methylpropargylamine (8)

2,5-Dihydroxyacetophenone, 2.0 grams (13.14 mmoles), was treated with 1.1 ml (13.75 mmoles) chloroacetone and 2.0 grams potassium carbonate in 50 ml acetonitrile under reflux for 20 hours. Then the mixture was filtered and the filtrate was stripped in vacuo. The residue was chromatographed on silica gel using methylene chloride as eluent to give 2.3 grams of a mixture consisting of 5:1 mono- and bis-ether (3-acyl-4-hydroxy)phenoxypropanone.

(3-Acyl-4-hydroxy)phenoxypropanone, containing 20% of the bis-ether 0.8 grams (3.83 mmoles) was treated with 0.6 ml (4.3 mmoles) 3-chlorobenzyl bromide and 1.0 grams potassium carbonate in 15 ml acetonitrile at 25° C. for 40 hours, and then at reflux for 3 hours. Then it was filtered and the filtrate was stripped in vacuo. The residue was chromatographed on silica gel using 1:3 ethyl acetate/hexanes to give 1.2 grams [3'-Acyl-4'-(m-chlorophenylmethyloxy)phenoxy]-propanone at 94% yield.

[3'-Acyl-4'-(m-chlorophenylmethyloxy)phenoxy]-propanone, 0.6 grams (1.8 mmoles), was treated with 272.5 mg (2.0 mmoles) zinc chloride and 126 mg (2.0 mmoles) sodium cyanoborohydride and 0.17 ml (2.0 mmoles) methylpropargylamine in 25 ml methanol at 25° C. for 120 hours. Then the solvent was striped in vacuo and the residue was partitioned between 100 ml ethyl acetate and 50 ml water. The ethyl acetate was washed with 30 ml 1M sodium hydroxide solution and brine, dried, and stripped in vacuo. The residue was chromatographed on silica gel using 30% ethyl acetate/hexanes to give 400 mg of product (30). This was treated with hydrochloride acid to form the hydrochloride salt, mp 45°–46° C. Mass Spectrum: 386 (M+1, 100%).

EXAMPLE 9

1-[2'-Acyl-4'-(m-trifluoromethylphenylmethyloxy)-phenoxy]-3-methoxy-2-propanol (9)

2-Acyl-4-(m-trifluoromethylphenylmethyloxy)-phenol, 1.4 grams (3.85 mmoles), was treated with 0.4 ml (4.5 mmoles) of epibromohydrin, 1 gram potassium carbonate, and 100 mg potassium iodide under reflux in 20 ml acetonitrile for 48 hours. Then the mixture was diluted with 50 ml ethyl acetate and filtered. The filtrate was stripped in vacuo, to give 1.49 grams of a material that was used for the next reaction without purification.

The crude product from the above reaction was dissolved in 30 ml anhydrous methanol and treated with 619 mg 60% sodium hydride in oil at 0° C. and then stirred at 25° C. for 20 hours. Then the methanol was striped in vacuo and the residue was partitioned between 150 ml ethyl acetate and 60 ml water. The organic layer was washed with brine solution, dried, and stripped in vacuo. The residue was chromatographed on silica gel using 40% ethyl acetate/hexanes to give 0.91 grams product (26) at 59% yield for the two steps. Mp 57°–59° C. Elemental analysis. Calculated for $C_{20}H_{21}F_3O_5$: C 60.30, H 5.31, F 14.31; found: C 59.92, H 5.20, F 14.27.

EXAMPLE 10

S(+)-1-[2'-Acyl-4'-(m-trifluoromethylphenylmethyloxy)phenoxy]-3-methoxy-2-propanol (10)

2-Acyl-4-(m-trifluoromethylphenylmethyloxy)-phenol, 5.50 grams (17.73 mmoles), was treated with 700 mg (17.52 mmoles) 60% sodium hydride in oil in 30 ml dry N,N-dimethylformamide at 0° C. for 30 min and at 25° C. for 1 hour. Then 4.0 grams (17.52 mmoles) 2-(S+)glycidyl tosylate in 20 ml N,N-dimethylformamide was added and the reaction was stirred at 25° C. for 64 hours. Then it was partitioned between 200 ml ethyl acetate and 100 ml water. The aqueous layer was extracted with 200 ml ethyl acetate and the combined organic extracts were washed with brine solution, dried, and stripped in vacuo. The resulting product was used directly for the next reaction.

The crude epoxide from the previous reaction was treated with 1400 mg (36 mmoles) 60% sodium hydride in oil in 130 ml dry methanol at 0° C. for 1 hour, and at 25° C. for 64 hours. Then the methanol was stripped in vacuo and the residue was partitioned between 200 ml ethyl acetate and 100 ml water. The water layer was extracted 200 ml ethyl acetate and the combined organic extracts were washed with brine solution, dried, and the solvent was stripped in vacuo. The residue was chromatographed on silica gel using 4:5 ethyl acetate/hexanes to give 5.02 grams product (28) at 71% yield for the two steps. Mp 59°–61° C. Elemental analysis. Calculated for $C_{20}H_{21}F_3O_5$: C 60.30, H 5.31, F 14.31; found: C 60.18, H 5.18, F 14.30. $[a]D^{20} = +2.89°$ (c=1.00, $CH_2Cl_2$); 82% ee, as determined by HPLC (chiral column OB).

EXAMPLE 11

(S)-1-[2'-Acyl-4'-(m-trifluoromethylphenylmethyloxy)-phenoxy]-3-methoxy-2-propyl acetate (11)

1- [2'-Acyl-4'-(m-trifluoromethylphenylmethyloxy)-phenoxy]-3-methoxy-2-propanol, 0.5 grams (1.25 mmoles), was treated with 0.15 ml (2.1 mmoles) acetyl chloride in a mixture of 7 ml methylene chloride and 0.5 ml pyridine at 0° C. for 1 hour and then at 25° C. for 16 hours. Then the reaction mixture was partitioned between 100 ml ethyl acetate and 40 ml water. The organic layer was washed with 1M hydrochloric acid saturated aqueous sodium bicarbonate and brine solutions, dried, and stripped in vacuo. The residue was chromatographed on silica gel using 1:3 ethyl acetate/hexanes as eluent to give 0.506 grams of the title product at 91% yield, Mp 34°–36° C. Elemental analysis. Calculated for $C_{22}H_{23}F_3O_6$: C60.00, H 5.26, F 12.94; found: C 59.92, H 5.23, F 13.09. $[a]D^{20} = -13.25°$ (C=1.03, $CH_2Cl_2$)

EXAMPLE 12

(S)-1-[2'-Acyl-4'-(m-trifluoromethylphenylmethyloxy)-phenoxy]-3-methoxy-2-propyl methylcarbonate (12)

1-[2'-Acyl-4'-(m-trifluoromethylphenylmethyloxy)-phenoxy]-3-methoxy-2-propanol, 0.50 grams (1.25 mmoles), was treated with 0.15 ml (1.94 mmoles) methyl chloroformate and 50 mg (0.41 mmoles) 4-dimethylaminopyridine in a mixture of 7 ml methylene chloride and 0.5 ml pyridine at 0° C. for 1 hour and then at 25° C. for 48 hours. Then the reaction mixture was partitioned between 100 ml ethyl acetate and 30 ml water. The organic layer was washed with 1M hydrochloric acid, saturated aqueous sodium bicarbonate and brine solutions, dried, and stripped in vacuo. The residue was chromatographed on silica gel using 1:3 ethyl acetate/hexanes as eluent to give 0.15 grams of the title product at 26% yield, Mp 60°–61° C. Elemental analysis. Calculated for $C_{22}H_{23}F_3O_7$: C 57.89, H 5.08, F 12.49; found: C 58.08, H 4.98, F 12.51. $[a]_D^{20} = -15.34°$ (c=1.05, $CH_2Cl_2$).

The chemical properties of representative compounds of this invention are summarized in Table I.

TABLE I

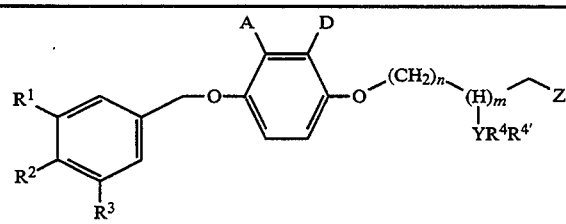

| Ex. No. | $R^1, R^2, R^3$ | Y, R4, R4' | A | D | Z | n | m | MP °C. |
|---|---|---|---|---|---|---|---|---|
| 1 | Cl, H, H | | H | CHO | CN | 2 | 0 | 75–77 |
| 2 | Cl, H, H | | H | $CH_2OMe$ | CN | 2 | 0 | 66–68 |
| 3 | Cl, H, H | | H | $CO_2Me$ | CN | 2 | 0 | 97–98 |
| 4 | Cl, H, H | | H | COMe | CN | 2 | 0 | 65–66 |
| 5 | Cl, H, H | | COMe | H | CN | 2 | 0 | L |
| 6 | $CF_3$, H, $CF_3$ | | H | COMe | CN | 2 | 0 | 110–112 |
| 7 | $CF_3$, H, H | | H | COMe | OH | 2 | 0 | 60–62 |
| 8 R, S | Cl, H, H | N, Me, $CH_2CCH$ | COMe | H | H | 1 | 1 | 45–46 |
| 9 R, S | $CF_3$, H, H | O, H | H | COMe | OMe | 1 | 1 | 57–59 |
| 10 S | $CF_3$, H, H | O, H | H | COMe | OMe | 1 | 1 | 59–61 |
| 11 S | $CF_3$, H, H | O, COMe | H | COMe | OMe | 1 | 1 | 34–36 |
| 12 S | $CF_3$, H, H | O, $CO_2Me$ | H | COMe | OMe | 1 | 1 | 60–61 |
| 13 | Cl, H, H | | H | CHO | CN | 0 | 0 | 74–75 |
| 14 | Cl, H, H | | H | $CO_2Me$ | CN | 0 | 0 | 93–95 |
| 15 | Cl, Cl, H | | COMe | H | CN | 2 | 0 | 66–68 |
| 16 | Cl, H, H | | H | COMe | CN | 3 | 0 | 41–42 |
| 17 | $CF_3$, H, H | | H | COMe | CN | 2 | 0 | >300 |
| 18 | Cl, Cl, H | | H | COMe | CN | 2 | 0 | 63–65 |
| 19 | Cl, H, H | N, Me, H | COMe | H | H | 1 | 1 | 105–107 |
| 20 | Cl, H, H | | H | COEt | CN | 2 | 0 | L |
| 21 | F, H, H | | H | COMe | CN | 2 | 0 | 62–64 |
| 22 | F, H, H | | H | COEt | CN | -2 | 0 | 54–56 |
| 23 | OMe, H, H | | H | COMe | CN | 2 | 0 | 40–44 |
| 24 | Me, Me, H | | H | COMe | CN | 2 | 0 | 61–66 |
| 25 | H, H, H | | H | COMe | CN | 2 | 0 | 50–53 |
| 26 | OMe, H, OMe | | H | COMe | CN | 2 | 0 | 54–56 |
| 27 | Me, H, H | | H | COMe | CN | 2 | 0 | 42–46 |
| 28 | Cl, H, H | | H | $CH_2OH$ | CN | 2 | 0 | L |
| 29 | Cl, H, H | | H | $CH_2OH$ | CN | 0 | 0 | L |
| 30 | Cl, H, H | | H | $CO_2Me$ | CN | 3 | 0 | L |
| 31 | F, H, H | | H | COMe | OH | 2 | 0 | 84–85 |
| 32 | Cl, H, H | | H | COMe | OH | 2 | 0 | L |
| 33 | H, F, H | | H | COEt | CN | 1 | 0 | L |
| 34 R, S | Cl, H, H | O, H | H | COMe | OMe | 1 | 1 | 50–52 |
| 35 | F, H, H | O, H | H | COMe | OMe | 1 | 1 | L |
| 36 S | Cl, H, H | O, H | H | COMe | OMe | 1 | 1 | 47–50 |
| 37 R | $CF_3$, H, H | O, H | H | COMe | OMe | 1 | 1 | 58–60 |
| 38 R | $CF_3$, H, H | O, COMe | H | COMe | OMe | 1 | 1 | 34–36 |
| 39 R | $CF_3$, H, H | O, $CO_2Me$ | H | COMe | OMe | 1 | 1 | 60–61 |
| 40 | CN, H, H | | H | COMe | CN | 2 | 0 | |
| 41 | $NO_2$, H, H | | H | COMe | CN | 2 | 0 | |
| 42 | $C_2F_5$, H, H | | H | COMe | CN | 2 | 0 | |
| 43 | Cl, H, H | | H | CONHMe | CN | 2 | 0 | |
| 44 | Cl, H, H | | H | CN | CN | 2 | 0 | |

L = Liquid
36: $[a]_D^{20}$ = +3.09° (c = 1.00, $CH_2Cl_2$); 81% ee, as determined by HPLC (chiral column OB).
37: $[a]_D^{20}$ = -3.19° (c = 1.00, $CH_2Cl_2$); 81% ee, as determined by HPLC (chiral column OB).
38: $[a]_D^{20}$ = +14.53° (c = 1.00, $CH_2Cl_2$).
39: $[a]_D^{20}$ = +18.52° (c = 1.02, $CH_2Cl_2$).

UTILITY

The compounds of this invention are generally utilized as the free base or as the acid addition salts. Such salts may be prepared by methods well known in the art.

They are formed with both inorganic or organic acids, for example: maleic, fumaric, benzoic, ascorbic, benzenesulfonic, hydrochloric, and hydrobromic.

The compounds of the present invention are useful in the inhibition of monoamine oxidases. They are particularly useful in the inhibition of monoamine oxidase B. The activity of the compounds of the present invention was demonstrated by the test described in the J. Neurochem., 1983, 40, 1534, which is herein incorporated by reference. This test measures the in vitro inhibitory action of the two types A and B monoamine oxidase in rat brain tissue. The results, shown in Table II, demonstrate that the compounds of the present invention will have utility in the treatment of diseases involving or related to monoamine oxidase inhibition. Finally, it is expected that the compounds of the present invention may be useful in treating neurological disorders including memory disorders, cognitive dysfunction, dementia, dementia of the Alzheimer's type, Parkinson's syndrome, depression, hyperactive syndrome, schizophrenia, and changes in temperament.

The $IC_{50}$ values were obtained by measuring the inhibitory activity of the corresponding compounds on a 200 mM solution Phenethylamine[14-C] for MAO B and on a 1.0 mM solution 5-Hydroxytryptamine[14-C] for MAO A.

PHARMACEUTICAL COMPOSITIONS

The compounds of the invention can be administered in a variety of pharmaceutical preparations well known to those skilled in the pharmaceutical art. For parenteral administration, the compounds can be prepared in aqueous injection solutions (sterile) which can contain antioxidants, buffers, bacteriostats, and other additives commonly employed in such solutions. Extemporaneous injection solutions can be prepared from sterile pills, granules or tablets which can contain diluents, dispersing and surface active agents, binders and lubricants, as well as the compound of the invention.

In the case of oral administration, fine powders or granules of the compound of the invention can be formulated with diluents and dispersing and surface active

TABLE II

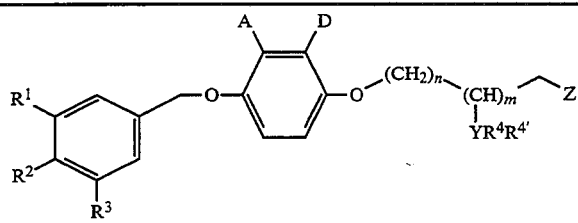

| Ex. No. | $R^1, R^2, R^3$ | Y, R4, R4' | A | D | Z | n | m | MAO B $IC_{50}$ | A/B |
|---|---|---|---|---|---|---|---|---|---|
| 1 | Cl, H, H | | H | CHO | CN | 2 | 0 | $3 \times 10^{-8}$ | 100 |
| 2 | Cl, H, H | | H | $CH_2OMe$ | CN | 2 | 0 | $3 \times 10^{-7}$ | 33 |
| 3 | Cl, H, H | | H | $CO_2Me$ | CN | 2 | 0 | $6 \times 10^{-6}$ | |
| 4 | Cl, H, H | | H | COMe | CN | 2 | 0 | $3 \times 10^{-8}$ | 333 |
| 5 | Cl, H, H | | COMe | H | CN | 2 | 0 | $1 \times 10^{-6}$ | |
| 6 | $CF_3$, H, $CF_3$ | | H | COMe | CN | 2 | 0 | $1 \times 10^{-7}$ | >10000 |
| 7 | $CF_3$, H, H | | H | COMe | OH | 2 | 0 | $3 \times 10^{-8}$ | 1667 |
| 8 * | Cl, H, H | N, Me, $CH_2CCH$ | COMe | H | H | 1 | 1 | $3 \times 10^{-9}$ | <300 |
| 9 * | $CF_3$, H, H | O, H | H | COMe | OMe | 1 | 1 | $2 \times 10^{-8}$ | 2000 |
| 10 S | $CF_3$, H, H | O, H | H | COMe | OMe | 1 | 1 | | |
| 11 S | $CF_3$, H, H | O, COMe | H | COMe | OMe | 1 | 1 | | |
| 12 S | $CF_3$, H, H | O, $CO_2Me$ | H | COMe | OMe | 1 | 1 | | |
| 13 | Cl, H, H | | H | CHO | CN | 0 | 0 | $3 \times 10^{-7}$ | <10 |
| 14 | Cl, H, H | | H | $CO_2Me$ | CN | 0 | 0 | $1 \times 10^{-6}$ | |
| 15 | Cl, Cl, H | | COMe | H | CN | 2 | 0 | $8 \times 10^{-7}$ | |
| 16 | Cl, H, H | | H | COMe | CN | 3 | 0 | $7 \times 10^{-7}$ | |
| 17 | $CF_3$, H, H | | H | COMe | CN | 2 | 0 | $2 \times 10^{-8}$ | <50 |
| 18 | Cl, Cl, H | | H | COMe | CN | 2 | 0 | $1 \times 10^{-7}$ | <10 |
| 19 * | Cl, H, H | N, Me, H | COMe | H | H | 1 | 1 | $7 \times 10^{-6}$ | |
| 20 | Cl, H, H | | H | COEt | CN | 2 | 0 | $4 \times 10^{-7}$ | |
| 21 | F, H, H | | H | COMe | CN | 2 | 0 | $1 \times 10^{-7}$ | 100 |
| 22 | F, H, H | | H | COEt | CN | 2 | 0 | $8 \times 10^{-7}$ | |
| 23 | OMe, H, H | | H | COMe | CN | 2 | 0 | $2 \times 10^{-7}$ | 300 |
| 24 | Me, Me, H | | H | COMe | CN | 2 | 0 | $4 \times 10^{-7}$ | >2500 |
| 25 | H, H, H | | H | COMe | CN | 2 | 0 | $5 \times 10^{-7}$ | 100 |
| 26 | OMe, H, OMe | | H | COMe | CN | 2 | 0 | $3 \times 10^{-7}$ | 10 |
| 27 | Me, H, H | | H | COMe | CN | 2 | 0 | $1 \times 10^{-7}$ | 300 |
| 28 | Cl, H, H | | H | $CH_2OH$ | CN | 2 | 0 | $1 \times 10^{-6}$ | |
| 29 | Cl, H, H | | H | $CH_2OH$ | CN | 0 | 0 | $2 \times 10^{-6}$ | |
| 30 | Cl, H, H | | H | $CO_2Me$ | CN | 3 | 0 | $8 \times 10^{-5}$ | |
| 31 | F, H, H | | H | COMe | OH | 2 | 0 | $1 \times 10^{-7}$ | 100 |
| 32 | Cl, H, H | | H | COMe | OH | 2 | 0 | $1 \times 10^{-7}$ | 400 |
| 33 | H, F, H | | H | COEt | CN | 2 | 0 | $>1 \times 10^{-4}$ | |
| 34 * | Cl, H, H | O, H | H | COMe | OMe | 1 | 1 | $5 \times 10^{-8}$ | 600 |
| 35 * | F, H, H | O, H | H | COMe | OMe | 1 | 1 | $3 \times 10^{-7}$ | 233 |
| 36 S | Cl, H, H | O, H | H | COMe | OMe | 1 | 1 | $9 \times 10^{-8}$ | 444 |
| 37 R | $CF_3$, H, H | O, H | H | COMe | OMe | 1 | 1 | | |
| 38 R | $CF_3$, H, H | O, COMe | H | COMe | OMe | 1 | 1 | | |
| 39 R | $CF_3$, H, H | O, $CO_2Me$ | H | COMe | OMe | 1 | 1 | | |

* = racemic mixture agents, and can be prepared in water, a syrup, capsules, cachets, a non aqueous suspension or an emulsion. In dry forms optional binders and lubricants can be present. The compositions may also include flavorants, preservatives, suspending, thickening and emulsifying agents and other pharmaceutically acceptable additives. For rectal administration, the compounds can be presented in the form of suppositories containing the bases usually employed for suppositories.

The pharmaceutical compositions of the invention, which can be used in the method of producing inhibition of MAO in general and MAO B in particular, comprise a pharmaceutically acceptable carrier and, as the active ingredient, at least one of the above described substituted hydroquinone ethers. The active ingredient is present in a dosage unit composition in an amount sufficient to produce MAO inhibition. Preferably, the pharmaceutical compositions of the invention include the active ingredient in a quantity selected from 1 mg to 500 mg, advantageously, from 2 mg to 100 mg per dosage unit. Appropriate concentrations and dosage unit sizes can be readily determined by one skilled in the art.

Capsules

A large number of unit capsules are prepared by filling standard two-piece hard gelatin capsules each with 50 mg of powdered active ingredient, 175 mg of lactose, 24 mg of talc, and 6 mg of magnesium stearate.

Soft Gelatin Capsules

A mixture of active ingredient in soybean oil is prepared and injected by means of a positive displacement pump into gelatin to form soft gelatin capsules containing 50 mg of the active ingredient. The capsules are washed in petroleum ether and dried.

Tablets

A large number of tablets are prepared by conventional procedures so that the dosage unit is 50 mg of active ingredient, 6 mg of magnesium stearate, 70 mg of microcrystalline cellulose, 11 mg of cornstarch, and 225 mg of lactose. Appropriate coatings may be applied to increase palatability or delay absorption.

Suspension

An aqueous suspension is prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection is prepared by stirring 1.5% by weight of active ingredient in 10% by volume propylene glycol and water. The solution is sterilized by commonly used techniques.

Nasal Spray

An aqueous solution is prepared such that each 1 mL contains 10 mg of active ingredient, 1.8 mg methylparaben, 0.2 mg propylparaben and 10 mg methylcellulose. The solution is dispensed into 1 mL vials.

Lung Inhaler

A homogeneous mixture of the active ingredient in polysorbate 80 is prepared such that the final concentration of the active ingredient will be 10 mg per container and the final concentration of polysorbate 80 in the container will be 1% by weight. The mixture is dispensed into each can, the valves are crimped onto the can and the required amount of dichlorotetrafluoroethane is added under pressure.

Ointment

The active ingredient is added to a mixture of 48% by weight white petroleum, 10% liquid petroleum, 8% glycerol monostearate, 3% isopropyl myristate, and 20% llanolin at 70° C. After thorough mixing, a warm solution of methyl and propyl parabens in water containing sodium acetone bisulfite is added such that the final concentrations of each paraben is 0.15%, of water is 8%, and of sodium acetone bisulfite is 0.5%. The mixture is stirred until it has reached room temperature.

We claim:

1. A compound having the formula:

$$\text{(I)}$$

and pharmaceutically acceptable salts thereof, wherein:

X is $R^1$, $R^2$, and $R^3$, are independently selected from the group consisting of hydrogen, halogen, $C_1$–$C_4$ alkyl, $C_1$–$C_4$ alkoxy, $CF_3$, $C_2F_5$, CN, and $NO_2$;

A and D are independently selected from the group including hydrogen, $COR^5$, $CH_2OR^6$ and CN;

Y is a nitrogen or oxygen atom;

$R^4$ and $R^{4'}$ are independently selected from the group consisting of hydrogen, $C_1$–$C_4$ alkyl, allyl, propargyl, and $COR^8$, provided that when Y is oxygen $R^3$ is hydrogen or $COR^8$, and $R^{4'}$ is not present;

Z is hydrogen, CN, OH, $OR^6$, $OCOR^6$, $OCO_2R^6$, or $OCONR^6R^7$;

$R^5$ is hydrogen, $C_1$–$C_4$ alkyl, or $C_1$–$C_4$ alkoxy, or $C_1$–$C_4$ dialkylamino;

$R^6$ and $R^7$ independently are selected from the group consisting of hydrogen and $C_1$–$C_4$ alkyl;

$R^8$ is $C_1$–$C_4$ alkyl, $C_1$–$C_4$ alkoxy, or $C_1$–$C_4$ alkylamino, or $C_2$–$C_8$ dialkylamino;

m is 0 or 1; and n is 1–5, provided that when n=2–5, then m=0;

provided that when:

$R^1$, $R^2$, and $R^3$ are H;

A is H;

D is $CO_2CH_3$, $COCO_2H$, $COCH_3$, CN, or $CONH_2$;

n=0–3; and m=0; then Z cannot be $CO_2CH_2CH_3$, $CO_2H$, or $OCH_3$.

2. A compound of claim 1 wherein:

$R^1$, $R^2$, and $R^3$ are independently selected from the group consisting of H, F, Cl, Br, I, $CH_3$, $OCH_3$, $CF_3$, CN, and $NO_2$;

A and D are independently selected from the group consisting of H, $COR^5$, $CONR_2^6$ and $CH_2OR^6$, provided that either A or D is H and that A and D cannot both be H;

Y is a nitrogen or oxygen atom;

$R^4$ and $R^{4'}$ are independently selected from the group consisting of H, $CH_3$, propargyl, and $COR^8$ provided that when Y is oxygen $R^4$ is H or $COR^8$, and $R^{4'}$ is not present;

Z is H, CN, OH, $OCOR^6$, $OCO_2R^6$, or $OCONR^6R^7$;

$R^5$ is H, $CH_3$, $C_2H_5$, $OCH_3$, $OC_2H_5$, $N(CH_3)_2$, $N(C_2H_5)_2$;

$R^6$ is H, $CH_3$, or $C_2H_5$;

$R^8$ is $CH_3$, $C_2H_5$, $OCH_3$, $OC_2H_5$, $N(CH_3)_2$, $N(C_2H_5)_2$;

m is 0 or 1;

n is 1–5, provided that when n=2–5, then m=0.

3. The compound of claim 1 selected from the group: 4-[2'-Formyl-4'-(m-chlorophenylmethyloxy)phenoxy]-butyronitrile; 4-[2'-Methoxymethyl-4'-(m-chlorophenylmethyloxy)phenoxy]butyronitrile; 4-[2'-Carbomethoxy-4'-(m-chlorophenylmethyloxy)phenoxy]-butyronitrile; 4-[2'-Acyl-4'-(m-chlorophenylmethyloxy)phenoxy]butyronitrile; 4-[3'-Acyl-4'-(m-chlorophenylmethyloxy)phenoxy]butyronitrile; 4-{2'-Acetyl-4'-[(3",5"-bis-trifluoromethylphenyl)-methyloxy]-phenoxy}butyronitrile; 3-[2'-Acyl-4'-(m-trifluoromethylphenylmethyloxy)phenoxy]propanol; N-2-[3'-Acyl-4'-(m-chlorophenylmethyloxy)phenoxy]-1-methylethyl-N-methylpropargylamine; 1- [2'-Acyl-4'-(m-trifluoromethylphenylmethyloxy)phenoxy]-3-methoxy-2-propanol; S(+)-1-[2'-Acyl-4'-(m-trifluoromethylphenylmethyloxy)phenoxy]-3-methoxy-2-propanol; (S)-1-[2'-Acyl-4'-(m-trifluoromethylphenylmethyloxy)-phenoxy]-3-methoxy-2-propyl acetate; (S)-1-[2'-Acyl-4'-(m-trifluoromethylphenylmethyloxy)phenoxy]-3-methoxy-2-propyl methylcarbonate;

4. A method of treating diseases involving monoamine oxidase in a mammal comprising administering to a mammal in need of such treatment a monoamine oxidase inhibiting effective amount of a compound of claim 1.

5. A method of treating diseases involving monoamine oxidase in a mammal comprising administering to a mammal in need of such treatment a monoamine oxidase inhibiting effective amount of a compound of claim 2.

6. A method of treating diseases involving monoamine oxidase in a mammal comprising administering to a mammal in need of such treatment a monoamine oxidase inhibiting effective amount of a compound of claim 3.

7. The method of claim 4 wherein the monoamine oxidase is monoamine oxidase B.

8. The method of claim 5 wherein the monoamine oxidase is monoamine oxidase B.

9. The method of claim 6 wherein the monoamine oxidase is monoamine oxidase B.

10. A pharmaceutical composition comprising a pharmaceutically acceptable carrier and a monoamine oxidase inhibiting effective amount of a compound of claim 1.

11. A pharmaceutical composition comprising a pharmaceutically acceptable carrier and a monoamine oxidase inhibiting effective amount of a compound of claim 2.

12. A pharmaceutical composition comprising a pharmaceutically acceptable carrier and a monoamine oxidase inhibiting effective amount of a compound of claim 3.

* * * * *